United States Patent

Kodama et al.

[11] 3,972,882
[45] Aug. 3, 1976

[54] SYM.-TRIAZINE CARBAMATES

[75] Inventors: Yutaka Kodama; Tsutomu Kodama; Akira Takai, ; Masaakira Senoura; Isao Watanabe; Katsunori Tanaka; Tomonobu Yamaguchi; Norio Abe; Takuya Kodama, all of Toyama, Japan

[73] Assignee: Toyama Chemical Co., Ltd., Tokyo, Japan

[22] Filed: Nov. 6, 1974

[21] Appl. No.: 521,370

[30] Foreign Application Priority Data
Nov. 9, 1973 Japan.............................. 48-125466

[52] U.S. Cl................................ 260/249.5; 424/249
[51] Int. Cl.². ..................................... C07D 251/46
[58] Field of Search ................................ 260/249.5

[56] References Cited
UNITED STATES PATENTS

| 3,244,712 | 4/1966 | Knusli et al. | 260/249.5 X |
|---|---|---|---|
| 3,255,191 | 6/1966 | Dexter et al. | 260/249.5 X |
| 3,296,263 | 1/1967 | Tsujikawa | 260/249.5 |

Primary Examiner—John M. Ford
Attorney, Agent, or Firm—Oblon, Fisher, Spivak, McClelland & Maier

[57] ABSTRACT

Novel sym.-triazines having the formula:

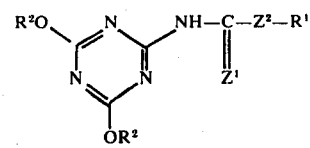

wherein $R^1$ is a substituted or unsubstituted alkyl, alkenyl, cycloalkyl, cycloalkylalkyl, aralkyl or heterocyclic alkyl group; $R^2$ is a hydrogen atom or a substituted or unsubstituted alkyl, alkenyl, cycloalkyl, cycloalkylalkyl, aryl, aralkyl or heterocyclic alkyl group; and $Z^1$ and $Z^2$, which may be the same or different, each represents oxygen or sulfur, have a central nerve inhibitory activity, an anti-inflammatory activity, an analgesic activity and a sedative activity, and can be prepared by reacting a 2,4-dichloro-6-substituted sym.-triazine with a compound having the formula $HO-R^2$ in which $R^2$ is the same as defined above.

18 Claims, No Drawings

SYM.-TRIAZINE CARBAMATES

This invention relates to novel sym.-triazines of the general formula (I) having an anti-inflammatory activity, an analgesic activity, a central nerve inhibitory activity and a sedative activity, and to a process for preparing the same.

According to this invention, there is provided novel sym.-triazines represented by the formula:

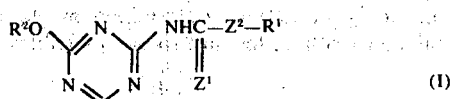

wherein $R^1$ is a substituted or unsubstituted alkyl, alkenyl, cycloalkyl, cycloalkylalkyl, aralkyl, or heterocyclic alkyl group; $R^2$ is hydrogen or a substituted or unsubstituted alkyl, alkenyl, cycloalkyl, cycloalkylalkyl, aryl, aralkyl or heterocyclic alkyl group; and $Z^1$ and $Z^2$, which may be the same or different, each represents oxygen or sulfur, and also a process for preparing the above sym.-triazines (I), characterized by reacting a 2,4-dichloro-6-substituted sym.-triazine represented by the formula:

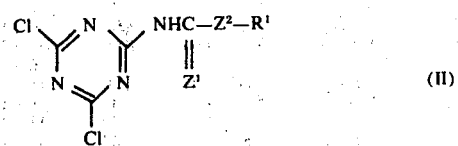

wherein $R^1$, $Z^1$ and $Z^2$ are the same as defined above, with a compound having the formula, $HO-R^2$ (III) in which $R^2$ is the same as defined above.

The sym.-triazines (I) of this invention are useful as anti-inflammatory agents, analgesics and sedatives.

The production of the sym.-triazine of this invention can be shown by the following reaction formulas:

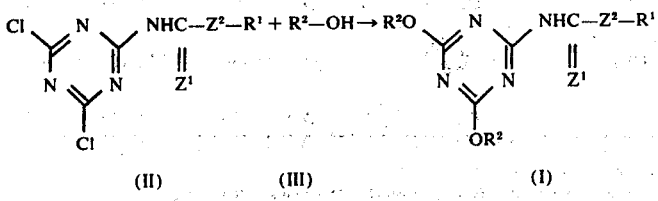

The starting compound (II) used in this invention can easily be prepared according to, for example, the following reaction formulas (see Y. Kodama et al., Journal of Synthetic Organic Chemistry, Japan, 22 467, 669 (1964), 23 57 (1965), and Japanese Patent Publication No. 47,395/72):

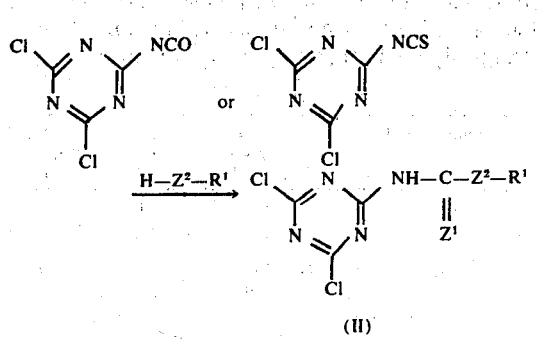

wherein $R^1$, $Z^1$ and $Z^2$ are the same as defined above. The substituents of $R^1$ in the formula (II) may be halogen atoms, $C_{1-4}$alkyl groups, nitro group, $C_{1-4}$-alkoxy groups, $C_{1-4}$alkylenedioxy groups and $C_{1-4}$alkylthio groups. Preferable examples of $R^1$ in the formula (II) are unsubstituted or said-group substituted $C_{1-5}$alkyl, $C_{1-5}$alkenyl, $C_{3-7}$cycloalkyl, $C_{3-7}$cycloalkyl-$C_{1-4}$alkyl, ar-$C_{1-4}$alkyl, and oxygen, sulfur or nitrogen-containing heterocyclic $C_{1-4}$alkyl groups.

The compound (III) to be used in this invention includes water, substituted and unsubstituted alkanols, cycloalkanols, cycloalkylalkanols, arylhydroxy compounds, aralkanols and heterocyclic alkanols (the substitutents of these substituted compounds may be halogen atoms, $C_{1-4}$-alkyl groups, nitro group, $C_{1-4}$alkoxy groups $C_{1-4}$alkylenedioxy groups, $C_{1-4}$alkylthio groups, and the like), and representative thereof are methyl alcohol, ethyl alcohol, n-propyl alcohol, isopropyl alcohol, n-butyl alcohol, isobutyl alcohol, isoamyl alcohol, n-hexyl alcohol, n-nonyl alcohol, methoxyethyl alcohol, ethylene chlorohydrin, furfuryl alcohol, tetrahydrofurfuryl alcohol, allyl alcohol, cyclopropanol, cyclobutanol, cyclopentanol, cyclohexanol, -methylcyclohexanol, 3,3-dimethylcyclohexanol, 3,3,5-trimethylcyclohexanol, cyclopropylmethyl alcohol, cyclobutylmethyl alcohol, phenol, 3-methylphenol, 3-chlorophenol, 4-methylphenol, 4-chlorophenol, 4-methoxyphenol, (4-methylthio)phenol, 4-bromophenol, 4-ethylphenol, 3-methoxyphenol, 3-bromophenol, (3-methylthio)phenol, 3,4-dimethylphenol, 3,5-dimethylphenol, 3,5-dimethyl-4-chlorophenol, benzyl alcohol, 4-methylbenzyl alcohol, 1-phenylethyl alcohol and the like.

In effecting the above reaction, an acid binding agent is preferably used. The acid binding agent includes, for example, alcoholates, phenolates, hydroxides, carbonates and hydrogen carbonates of alkali metals and alkaline earth metals, and organic amines such as pyridine, quinoline, picoline, trimethylamine, triethylamine, tributylamine, dimethylaniline and the like.

In carrying out the process of this invention, the above compound (III) may be allowed to serve as a solvent, or a non-hydroxy compound such as benzene, toluene, xylene, acetone, dioxane, diethyl ether, ethyl isopropyl ether, tetrahydrofuran, acetonitrile, chloroform or the like may be used as a solvent. A mixed solvent of two or more said compounds may be used.

The starting compound (II) is reacted while stirring with the above compound (III) in the above solvent, preferably in the presence of the acid binding agent. In this reaction, the amount of the compound (III) is usually at least 2 moles per mole, or excess moles, of the compound (II) or the amount of the acid binding agent to be employed is 2 moles per mole of the starting compound (II), and when the substituent of the starting compound (II) is an alkoxythiocarbonylamino group ($-NHC(S)OR^1$) or a substituted dithiocarbonylamino group ($-NHC(S)SR^1$), which relatively easily form a salt with the acid binding agent, the acid binding agent may preferably be used in 1 mole excess of said amount.

The reaction temperature and the reaction time may vary depending upon the kinds of the starting compound (II), the acid binding agent and the compound (III), though the reaction is usually effected at −50° to +150°C within 15 hours, preferably at 0° to 100°C for 10 minutes to 7 hours.

When, after the reaction, the objective compound (I) precipitates in the reaction solution, it is filtered, washed with water and then dried to recover the objective compound from the reaction solution. When the objective compound (I) is dissolved in the reaction solution, the solvent is removed by distillation, and water is added to the residue to separate the objective compound (I), which is then treated in the same manner as above. If when water is added, the objective compound (I) forms a salt with the acid binding agent to dissolve in water, the resulting solution is neutralized to deposit crystals, which are then treated in the same manner as above, or extracted with a hydrophobic solvent, for example, chloroform, benzene, toluene or the like, after which the solvent layer is separated from the aqueous layer, washed with water and then subjected to distillation to remove the solvent, thereby obtaining the objective compound (I) in the form of crude crystals. The thus obtained crude crystals of the objective compound (I) are usually recrystallized from a suitable inert solvent, for example, n-hexane, benzene, toluene or the like, to obtain pure product of the objective compound (I).

The compound (I) obtained by the above-mentioned process is a novel compound which has never been disclosed in any literature references, and hence, the structure thereof has been confirmed by an elementary analysis and an infrared absorption spectrum analysis.

The compound (I) has a very strong central nerve inhibitory activity and an anti-inflammatory, analgesic activity, and hence, is useful as a pharmaceutical product.

Representative examples of the sym.-triazines of this invention and their anti-carrageenin oedema activity and analgesic activity determined by the acetic acid-induced writhing test are shown in Tables 1 and 2.

Table 1

Anti-carregeenin oedema activity [According to the Winter method [Proc. Soc. exp. Biol. Med., 111 544 (1962)], a test compound suspended in the solution including 0.3 % of Tween-80 (a trade name of Atlas Powder Co., U.S.A.) was orally administered to a group of 5 male rats weighing 120 to 140 g.]

| No. | Compound (I) R¹ | R² | Z¹ | Z² | Dose (mg/kg) p.o. | Inhibition of oedema (%) *1 Peak (hr) | *2 Mean |
|---|---|---|---|---|---|---|---|
| 1 | CH₃ | CH₃ | O | O | 70<br>200<br>500 | 51.0 (2)<br>64.0 (2)<br>61.4 (2) | 44.6<br>49.5<br>52.8 |
| 2 | CH₂CH₃ | CH₃ | O | O | 70<br>200<br>500 | 36.3 (2)<br>48.0 (2)<br>78.8 (2) | 28.2<br>34.4<br>67.4 |
| 3 | CH₃ | CH₃ | S | O | 70<br>200<br>500 | 37.2 (2)<br>68.8 (2)<br>78.3 (2) | 24.7<br>46.7<br>61.0 |
| 4 | CH₂CH₃ | CH₃ | S | O | 70<br>200<br>500 | 23.9 (2)<br>45.9 (2)<br>64.5 (2) | 21.8<br>35.4<br>50.6 |
| 5 | (CH₂)₃CH₃ | CH₃ | S | O | 500 | 38.0 (2) | 18.1 |
| 6 | CH₂-⌬ | CH₃ | S | O | 500 | 16.3 (3) | — |
| 7 | CH₂CH₃ | CH₃ | S | S | 200<br>500 | 27.1 (5)<br>37.4 (2) | 17.6<br>27.6 |
| 8 | CH₃ | CH₂CH₃ | S | O | 500 | 32.2 (2) | 23.5 |
| 9 | CH₃ | ⌬ | S | O | 500 | 17.5 (2) | — |
| 10 | CH₂CH₃ | H | S | O | 500 | 13.0 (2) | — |

Note:
*1 Maximum oedema inhibition.
*2 Average oedema inhibition from 2 hrs to 5 hrs after the administration.

Table 2

Analgesic activity by the acetic acid-induced writhing test [According to the K. Takagi et al. method [Journal of the Pharmaceutical Society of Japan, 78 553 (1958)], a test compound suspended in the solution including 0.5 % of Tween-80 was orally administered to a group of 8 ddY male mice weighing 20 to 24 g.]

| No. | Compound (I) R¹ | R² | Z¹ | Z² | Dose (mg/kg) p.o. | Inhibition (%) | ED₅₀ (mg/kg) p.o. |
|---|---|---|---|---|---|---|---|
| 1 | CH₃ | CH₃ | O | O | 300<br>100 | 34.7<br>16.3 | >300 |
| 2 | CH₂CH₃ | CH₃ | O | O | 300<br>100 | 50.3<br>2.9 | 300 |

-continued

| No. | R¹ | Compound (I) R² | Z¹ | Z² | Dose (mg/kg) p.o. | Inhibition (%) | $ED_{50}$ (mg/kg) p.o. |
|---|---|---|---|---|---|---|---|
| 3 | $CH_3$ | $CH_3$ | S | O | 100<br>33.3<br>11.1<br>3.7 | 77.2<br>69.4<br>67.9<br>11.9 | 8.0 |
| 4 | $CH_2CH_3$ | $CH_3$ | S | O | 100<br>33.3<br>11.1<br>3.7 | 96.9<br>94.4<br>89.4<br>7.6 | 6.6 |
| 5 | $(CH_2)_3CH_3$ | $CH_3$ | S | O | 100<br>33.3 | 68.4<br>16.5 | 67.5 |
| 7 | $CH_2CH_3$ | $CH_3$ | S | S | 300<br>100<br>33.3 | 87.1<br>53.3<br>22.1 | 88.5 |
| 11 | $CH_2CH_3$ | $CH_3$ | O | S | 300<br>100 | 50.1<br>21.0 | 300 |

As is clear from Tables 1 and 2, the sym.-triazines of this invention have excellent anti-inflammatory, analgesic activity, and the toxicity test results show that, for example, the No. 3 compound exhibited $LD_{50}$ p.o. of 1,050 mg/kg and $LD_{50}$ i.p. of 500 mg/kg, and the No. 4 compound exhibited $LD_{50}$ p.o. of 1,020 mg/kg and $LD_{50}$ i.p. of 490 mg/kg of mice. Therefore, the sym.-triazines of this invention are useful as an anti-inflammatory agent and analgesics.

The sym.-triazine of this invention may be formulated in liquid and solid dosage forms for both oral and parenteral administration. The formulation of compounds exhibiting such activity in association with pharmaceutical carriers or diluents is well known.

Solid dosage forms for oral administration include capsules, tablets, pills, powders and granules. In such solid dosage forms the active compound is admixed with at least one inert diluent such as sucrose, lactose, or starch. Such dosage forms can also contain additional substances other than inert diluents, for example, lubricating agents such as magnesium stearate. In the case of capsules, tablets and pills the dosage forms may also contain buffering agents. Tablets and pills can additionally be prepared with enteric coatings.

Liquid dosage forms of oral administration include pharmaceutically acceptable emulsions, solutions, suspensions, syrups and elixirs containing inert diluents commonly used in the art, such as water. Besides inert diluents, such compositions can also include adjuvants such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles include propylene glycol, polyethylene glycol, vegetable oils such as olive oil, and injectable organic esters such as preserving, wetting, emulsifying and dispersing agents. They may also be manufactured in the form of sterile solid compositions which can be dissolved in sterile water or some other sterile injectable medium immediately prior to use.

The dosage of active ingredient to be administered varies with the degree of activity of the compound being employed. Generally, dosage levels of 0.5 to 100 mg/kg of body weight are administered to mammals from 1 to 4 times daily to obtain effective relief of inflammation, pain and fever.

This invention is further explained in more detail below with reference to Examples, which are merely by way of illustration and not by way of limitation.

EXAMPLE 1

Production of methyl 2,4-dimethoxy-sym.-triazinylcarbamate [2,4-dimethoxy-6-(methoxycarbonyl amino)-sym.-triazine]

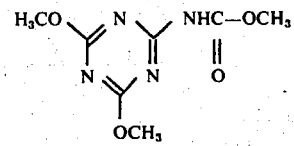

In 20 ml of methanol was dissolved 2.2 g (0.010 mole) of methyl 2,4-dichloro-sym.-triazinylcarbamate, and a solution of 0.64 g (0.028 mole) of metallic sodium in 30 ml of methanol was dropped thereinto while stirring at −5° to 0°C, after which the mixture was maintained at 15° – 20°C for 1.0 hr to complete the reaction. The solvent was removed by distillation under reduced pressure from the resulting reaction solution, and 30 ml of ice water was then added to the residue to dissolve the latter in the former. The resulting solution was treated with carbon, and 30 ml of chloroform was added thereto, after which the mixture was neutralized with diluted hydrochloric acid while stirring to a pH of 7. The chloroform layer was thereafter separated, washed with water and then dried, after which the chloroform was distilled off to obtain white methyl 2,4-dimethoxy-sym.-triazinylcarbamate. This was recrystallized from benzene to obtain 1.1 g (yield: 53%) of needle crystal having a melting point of 120° – 121°C.

| Elementary analysis (as $C_7H_{10}N_4O_4$) | | | |
|---|---|---|---|
| | C % | H % | N % |
| Found: | 39.30 | 4.63 | 26.20 |
| Calcd.: | 39.25 | 4.70 | 26.15 |

Infrared absorption spectrum: $\nu$N—H (3,350 cm$^{-1}$), $\nu$C=O (1,780 cm$^{-1}$), sym.-triazine ring (1,600, 1,570 810 cm$^{-1}$), and others (1,480, 1,350, 1,040 cm$^{-1}$).

The compounds shown in Table 3 were obtained in the same manner as in Example 1.

Table 3

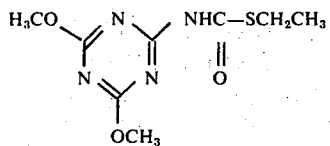

| R$^1$ | R$^2$ | Z$^1$ | Z$^2$ | Melting point (°C) |
|---|---|---|---|---|
| CH$_2$CH$_3$ | CH$_3$ | O | O | 77–78 |
| CH$_2$CH=CH$_2$ | CH$_3$ | O | O | 65–66 |

EXAMPLE 2

Production of ethyl 2,4-dimethoxy-sym.-triazinylthiolcarbamate [2,4-dimethoxy6-{(ethylthio)carbonylamino}-sym.-triazine]

In 20 ml of methanol was dissolved 2.5 g. (0.010 mole) of ethyl 2,4-dichloro-sym.-triazinylthiolcarbamate, and a solution of 0.69 g (0.030 mole) of metallic sodium in 30 ml of methanol was dropped thereinto while stirring at 0° – 5°C. The temperature was then slowly elevated, and the mixture was maintained at 20° – 30°C for 2 hrs to complete the reaction. The solvent was removed by distillation under reduced pressure from the resulting reaction solution, and the residue was dissolved in 30 ml of ice water and then treated with carbon, after which 30 ml of chloroform was added to the thus treated solution, and the resulting mixture was neutralized with diluted hydrochloric acid while stirring to a pH of 7. The chloroform layer was then separated, washed with water and then dried, after which the chloroform was removed by distillation to obtain white ethyl 2,4-dimethoxy-sym.-triazinylthiolcarbamate. This was recrystallized from a 1 : 1 (by volume) mixed solvent of n-hexane and benzene to obtain 1.1 g (yield: 45 %) of needle crystal melting at 107° – 108°C.

| Elementary analysis (as $C_8H_{12}N_4O_3S$) | | | |
|---|---|---|---|
| | C % | H % | N % |
| Found: | 39.30 | 4.89 | 22.89 |
| Calcd.: | 39.33 | 4.94 | 22.93 |

Infrared absorption spectrum: $\nu$N—H (3,200 cm$^{-1}$), $\nu$C=O (1,640 cm$^{-1}$), symo-triazine ring (1,580, 810cm$^{-1}$) and others (1,470, 1,370, 1,340, 1,230 cm$^{-1}$).

EXAMPLE 3 production of methyl 2,4-dimethoxy-sym.-triazinylthioncarbamate [2,4-dimethoxy-6-(methoxythiocarbonylamino)-sym.-triazine]

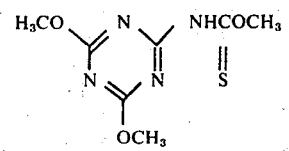

In 20 ml of methanol was dissolved 2.4 g (0.010 mole) of methyl 2,4-dichloro-sym.-triazinylthioncarbamate, and a solution of 0.73 g (0.032 mole) of metallic sodium in 30 ml of methanol was dropped thereinto while stirring at 0° – 5°C. The temperature was thereafter elevated and the mixture was maintained at 45° – 50°C for 3.5 hrs to complete the reaction. The methanol was removed from the resulting reaction solution by distillation under reduced pressure, and the residue was dissolved in 30 ml of water. The resulting solution was adjusted to a pH of 10 and then treated with carbon, after which 30 ml of chloroform was added thereto, and the resulting mixture was neutralized with diluted hydrochloric acid while stirring to a pH of 7. The chloroform layer was thereafter separated, washed with water and then dried, after which the chloroform was removed by distillation to obtain white methyl 2,4-dimethoxy-sym.-triazinylthioncarbamate. This was recrystallized from benzene to obtain 1.6 g (yield: 72 %) of needle crystal melting at 140° – 141°C.

| Elementary analysis (as $C_7H_{10}N_4O_3S$) | | | |
|---|---|---|---|
| | C % | H % | N % |
| Found: | 36.45 | 4.30 | 24.31 |
| Calcd.: | 36.50 | 4.37 | 24.32 |

Infrared absorption spectrum: $\nu$N—H (3,200 cm$^{-1}$), sym.-triazine ring (1,600, 1,540, 800 cm$^{-1}$), and others (1,490, 1,350, 1,320, 1,210 cm$^{-1}$).

The compounds shown in Table 4 were obtained in the same manner as in Example 3.

TABLE 4

| R$^1$ | R$^2$ | Z$^1$ | Z$^2$ | Melting point (°C) |
|---|---|---|---|---|
| CH$_2$CH$_3$ | CH$_3$ | S | O | 138–139 |
| CH(CH$_3$)$_2$ | CH$_3$ | S | O | 82–83 |
| CH$_2$CH=CH$_2$ | CH$_3$ | S | O | 120–121 |
| (CH$_2$)$_3$CH$_3$ | CH$_3$ | S | O | 129–130.5 |
| (CH$_2$)$_2$OCH$_3$ | CH$_3$ | S | O | 118–119 |
| –⟨H⟩ | CH$_3$ | S | O | 102–103 |
| CH$_2$–⟨⟩ | CH$_3$ | S | O | 136–137 |
| CH$_2$–⟨H/O⟩ | CH$_3$ | S | O | 84–85 |

EXAMPLE 4

Production of methyl 2,4-dimethoxy-sym.-triazinylthioncarbamate [2,4-dimethoxy-6-(methoxythiocarbonylamino)-sym.-triazine]

In 30 ml of methanol was dissolved 0.73 g (0.032 mole) of metallic sodium, and 2.4 g of methyl 2,4-dichloro-sym.-triazinylthioncarbamate was added while stirring to the resulting solution at 0° – 5°C. The temperature was then elevated, and the mixture was maintained at 40° – 50°C for 1 hr to complete the reaction. The methanol was removed from the resulting reaction solution by distillation under reduced pressure, and 30 ml of water was added to the residue to dissolve the latter in the former, and the resulting solution was adjusted to a pH of 10, thereafter treated with carbon, and then neutralized with diluted hydrochloric acid to a pH of 7, upon which white methyl 2,4-dimethoxy-sym.-triazinylthioncarbamate precipitated. This was filtered, washed with water, dried, and then recrystallized from benzene to obtain 1.9 g (yield: 82 %) of needle crystal melting at 140° – 141°C.

EXAMPLE 5

Production of ethyl 2,4-dimethoxy-sym.-triazinyldithiocarbamate [2,4-dimethoxy-6-{(ethylthio)thiocarbonylamino}-sym.-triazine]

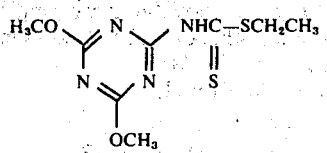

In 30 ml of methanol was dissolved 2.7 g (0.010 mole) of ethyl 2,4-dichloro-sym.-triazinyldithiocarbamate, and a solution of 1.3 g (0.032 mole) of sodium hydroxide in 30 ml of methanol was dropped into the resulting solution while stirring a 0° – 5°C. The temperature was thereafter elevated, and the mixture was maintained at 45° – 50°C for 3.5 hrs to complete the reaction. The methanol was removed from the thus obtained reaction solution by distillation under reduced pressure, and 30 ml of water was added to the residue to dissolve the latter in the former. The resulting solution was adjusted to a pH of 10, treated with carbon, and then neutralized with diluted hydrochloric acid to a pH of 7, upon which pale yellow ethyl 2,4-dimethoxy-sym.-triazinyldithiocarbamate deposited. This was filtered, washed with water, dried, and thereafter recrystallized from toluene to obtain 2.1 g (yield: 80 %) of needle crystal having a melting point of 153° – 154° C.

| | Elementary analysis (as $C_8H_{12}N_4O_2S_2$) | | |
|---|---|---|---|
| | C % | H % | N % |
| Found: | 36.95 | 4.66 | 21.61 |
| Calcd.: | 36.91 | 4.65 | 21.53 |

Infrared absorption spectrum. $\nu$N—H (3,160 cm$^{-1}$), sym.-triazine ring (1,610, 1,560, 1,490, 810 cm$^{-1}$), and others (1,460, 1,370, 1,350, 1,230, 1,133, 765 cm$^{-1}$).

EXAMPLE 6

Production of methyl 2,4-diethoxy-sym.-triazinylthioncarbamate [2,4-diethoxy-6-(methoxythiocarbonylamino)-sym.-triazine]

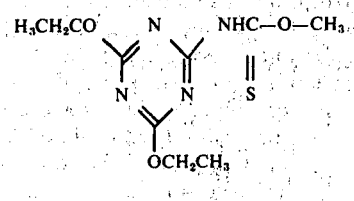

In 20 ml of ethanol was dissolved 2.4 g (0.010 mole) of methyl 2,4-dichloro-sym.-triazinylthioncarbamate, and a solution of 0.73 g (0.032 mole) of metallic sodium in 30 ml of ethanol was dropped into the resulting solution while stirring at 0° – 5°C. The temperature was thereafter elevated and the mixture was maintained at 45° – 50°C for 3.5 hrs to complete the reaction. The ethanol was removed from the thus obtained reaction solution by distillation under reduced pressure, and 20 ml of water was added to the residue to dissolve the latter in former, after which the resulting solution was adjusted to a pH of 10, and treated with carbon. To the thus treated solution was added 30 ml of chloroform, and the resulting mixture was neutralized with diluted hydrochloric acid while stirring to a pH of 7. The chloroform layer was separated, washed with water, dried, and then distilled to remove the chloroform to obtain white methyl 2,4-diethoxy-sym.-triazinylthioncarbamate. This was recrystallized from a n-hexane-benzene (1 : 1 by volume) mixed solvent to obtain 1.8 g (yield: 71 %) of needle crystal having a melting point of 100° – 101°C.

| | Elementary analysis (as $C_9H_{14}N_4O_3S$) | | |
|---|---|---|---|
| | C % | H % | N % |
| Found: | 41.80 | 5.42 | 21.70 |
| Calcd.: | 41.85 | 5.46 | 21.69 |

Infrared absorption spectrum: $\nu$N—H (3,200 cm$^{-1}$), sym.-triazine ring (1,600, 1,550, 1,520, 810 cm$^{-1}$), and others (1,320, 1,300, 1,200 cm$^{-1}$).

EXAMPLE 7

Production of methyl 2,4-diphenoxy-sym.-triazinylthioncarbamate [2,4-diphenoxy-6-(methoxythiocarbonylamino)-sym.-triazine]

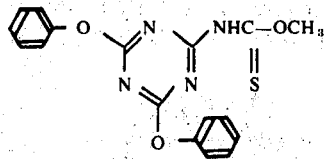

In 20 ml of ethanol was dissolved 2.4 g (0.010 mole) of methyl 2,4-dichloro sym.-triazinylthioncarbamate, and a solution of 0.73 g (0.032 mole) of metallic sodium and 2.8 g (0.030 mole) of phenol in 40 ml of ethanol was added dropwise to the resulting solution while stirring at 0° – 5°C. The temperature was elevated, and the mixture was maintained at 45° – 50°C for 3.5 hrs to complete the reaction. The ethanol was removed by distillation under reduced pressure from the thus obtained reaction solution, and 30 ml of water and 30 ml of chloroform were added to the residue, and the resulting solution was neutralized with diluted hydrochloric acid while stirring to a pH of 7. The chloroform layer was separated, washed with water, dried, and thereafter subjected to distillation to remove the chloroform, thereby obtaining white methyl 2,4-diphenoxy-sym.-triazinylthioncarbamate. This was recrystallized from toluene to obtain 2.6 g (yield: 75 %) of needle crystal melting at 167° – 170°C.

| | Elementary analysis (as $C_{17}H_{14}N_4O_3S$) | | |
|---|---|---|---|
| | C % | H % | N % |
| Found: | 59.55 | 3.89 | 15.78 |
| Calcd.: | 59.61 | 3.98 | 15.80 |

Infrared absorption spectrum: $\nu$N—H (3,180 cm$^{-1}$), sym.-triazine ring (1,580, 1,550, 1,500, 800 cm$^{-1}$), and others (1,370, 1,340, 1,310, 1,210, 1,180 cm$^{-1}$).

EXAMPLE 8

Production of methyl 2,4-diphenoxy-sym.-triazinylthioncarbamate [2,4-diphenoxy-6-(methoxythiocarbonylamino)-sym.-triazine]

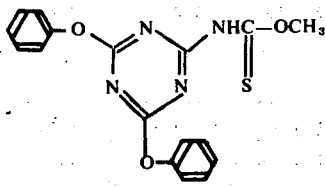

In 25 ml of acetone was dissolved 2.4 g (0.010 mole) of methyl 2,4-dichloro-sym.-triazinylthioncarbamate, and to the resulting solution was added dropwise a solution of 1.3 g (0.032 mole) of sodium hydroxide and 2.8 g (0.030 mole) in 25 ml of water while stirring at 0° – 5°C. The resulting mixture was maintained at 45° – 50°C for 3.0 hrs to complete the reaction. The resulting reaction solution was subjected to distillation under reduced pressure to remove the acetone therefrom, and 30 ml of water and 30 ml of chloroform were added to the residue. The resulting solution was treated in the same manner as in Example 7 to obtain white methyl 2,4-diphenoxy-sym.-triazinylthioncarbamate. This was recrystallized from toluene to obtain 2.7 g (yield: 76 %) of needle crystal having a melting point of 169° – 170°C.

EXAMPLE 9

Production of ethyl 2,4-dihydroxy-sym.-triazinylthioncarbamate, [2,4-dihydroxy-6-(ethoxythiocarbonylamino)-sym.-triazine]

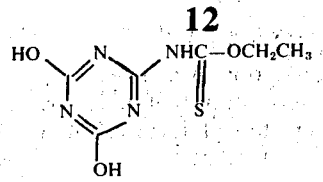

To a solution of 2.0 g (0.050 mole) of sodium hydroxide in 35 ml of water was added 2.5 g (0.010 mole) of ethyl 2,4-dichloro-sym.-triazinylthioncarbamate while stirring at 0° – 10°C, and the resulting solution was maintained at 45° – 50°C for 8 hrs to complete the reaction. The thus obtained reaction solution was treated with diluted hydrochloric acid to adjust the pH to 8, and then treated with carbon. The thus treated solution was then acidified to a pH of 3.5, upon which white ethyl 2,4-dihydroxy-sym.-triazinylthioncarbamate precipitated. This was filtered, washed with water, dried, and then recrystallized from acetic acid to obtain 1.3 g (yield: 62 %) of needle crystal which did not melt at a temperature of upto 250°C.

| | Elementary analysis (as $C_6H_8N_4O_3S$) | | |
|---|---|---|---|
| | C % | H % | N % |
| Found: | 33.29 | 3.93 | 25.95 |
| Calcd.: | 33.33 | 3.72 | 25.91 |

Infrared absorption spectrum: $\nu$N—H (3,100 cm$^{-1}$), $\nu$C = O (1,760, 1,680 cm$^{-1}$), sym.-triazine ring (1,620, 1,540, 810 cm$^{-1}$), and others (1,220, 1,200 cm$^{-1}$).

What is claimed is:

1. A compound of the formula:

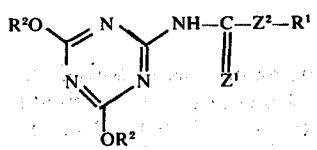

wherein R$^1$ is unsubstituted or a halogen-, C$_{1-4}$ alkyl-, nitro-, C$_{1-4}$ alkoxy-, C$_{1-4}$ alkylenedioxy- C$_{1-4}$ alkylthio-substituted C$_{1-5}$ alkyl, C$_{1-5}$ alkenyl, C$_{3-7}$ cycloalkyl, C$_{3-7}$ cycloalkyl C$_{1-4}$ alkyl, phenyl-C$_{1-4}$ alkyl or tetrahydrofurfuryl; R$^2$ is hydrogen, or unsubstituted halogen-, C$_{1-4}$ alkyl-, C$_{1-4}$ alkoxy-, or C$_{1-4}$ alkylthio-substituted C$_{1-4}$ alkyl or phenyl; and Z$^1$ and Z$^2$, which may be the same or different, each represents oxygen or sulfur.

2. Methyl 2,4-dimethoxy-sym.-triazinylthioncarbamate.
3. Ethyl 2,4-dimethoxy-sym.-triazinylthioncarbamate.
4. Methyl 2,4-dimethoxy-sym-triazinylcarbamate.
5. Ethyl 2,4-dimethoxy-sym-triazinylcarbamate.
6. Allyl 2,4-dimethoxy-sym-triazinylcarbamate.
7. Ethyl 2,4-dimethoxy-sym-triazinylthiolcarbamate.
8. Isopropyl 2,4-dimethoxy-sym-triazinylthioncarbamate.
9. Allyl 2,4-dimethoxy-sym-triazinylthioncarbamate.
10. n-Butyl 2,4-dimethoxy-sym-triazinylthioncarbamate.
11. Methoxy-ethyl 2,4-dimethoxy-sym-triazinylthioncarbamate.
12. Cyclohexyl 2,4-dimethoxy-sym-triazinylthioncarbamate.
13. Benzyl 2,4-dimethoxy-sym.-triazinylthioncarbamate.
14. Tetrahydrofurfuryl 2,4-dimethoxy-sym-triazinylthioncarbamate.

15. Ethyl 2,4-dimethoxy-sym-triazinyldithiocarbamate.
16. Methyl 2,4-diethoxy-sym-triazinylthioncarbamate.
17. Methyl 2,4-diphenoxy-sym-triazinylthioncarbamate.
18. Ethyl 2,4-dihydroxy-sym-triazinylthioncarbamate.

* * * * *